(12) United States Patent
Shaw et al.

(10) Patent No.: US 12,285,253 B2
(45) Date of Patent: Apr. 29, 2025

(54) BLOOD COLLECTION TUBE HOLDER WITH SINGLE NEEDLE

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 107 days.

(21) Appl. No.: 16/219,094

(22) Filed: Dec. 13, 2018

(65) Prior Publication Data

US 2019/0282147 A1    Sep. 19, 2019

Related U.S. Application Data

(60) Provisional application No. 62/644,211, filed on Mar. 16, 2018.

(51) Int. Cl.
*A61B 5/153* (2006.01)
*A61B 5/15* (2006.01)
*A61B 5/155* (2006.01)

(52) U.S. Cl.
CPC ........ *A61B 5/153* (2013.01); *A61B 5/150022* (2013.01); *A61B 5/15003* (2013.01);
(Continued)

(58) Field of Classification Search
CPC .............. A61B 5/153; A61B 5/150022; A61B 5/15003; A61B 5/150389; A61B 5/150473; A61B 5/150572; A61B 5/150656; A61B 5/150717; A61B 5/150732; A61B 5/150801; A61B 5/150908; A61B 5/155; A61B 5/1405; A61M 5/3202; A61M 5/3204; A61M 5/3213; A61M 5/3243; A61M 5/322; A61M 5/3221; A61M 5/3232; A61M 5/3234; A61M 2005/3224; A61M 2005/3227; A61M 2005/3228
See application file for complete search history.

(56) References Cited

U.S. PATENT DOCUMENTS 5,052,403 A    10/1991  Haber
5,810,775 A *   9/1998  Shaw ................. A61B 5/15003
                                                    600/576
(Continued)

FOREIGN PATENT DOCUMENTS

WO    2018009329    1/2018

*Primary Examiner* — Charles A Marmor, II
*Assistant Examiner* — Severo Antonio P Lopez
(74) *Attorney, Agent, or Firm* — Scheef & Stone, LLP; Robin L. Barnes; Michael J. Schofield

(57) ABSTRACT

A blood collection tube holder having a retractable single needle and a body comprising substantially parallel and laterally spaced apart barrel and needle retraction cavities separated by a partial wall that facilitates lateral movement of the single needle from the barrel cavity into alignment with the needle retraction cavity to initiate needle retraction. The barrel and a frontal attachment to the barrel are cooperatively configured to facilitate relative sliding movement between in a direction that is transverse to the longitudinal axis through the retractable single needle to initiate needle retraction.

19 Claims, 13 Drawing Sheets

(52) U.S. Cl.
CPC .. *A61B 5/150389* (2013.01); *A61B 5/150473* (2013.01); *A61B 5/150656* (2013.01); *A61B 5/150732* (2013.01); *A61B 5/150908* (2013.01); *A61B 5/1405* (2013.01); *A61B 5/150572* (2013.01); *A61B 5/150717* (2013.01); *A61B 5/150801* (2013.01); *A61B 5/155* (2013.01)

(56) References Cited

U.S. PATENT DOCUMENTS

| | | | |
|---|---|---|---|
| 6,280,401 B1 | 8/2001 | Mahurkar | |
| RE39,107 E | 5/2006 | Shaw | |
| 8,496,600 B2 | 7/2013 | Shaw et al. | |
| 9,247,899 B2 | 2/2016 | Shaw et al. | |
| 2010/0317999 A1* | 12/2010 | Shaw | A61M 5/3232 600/576 |
| 2014/0276435 A1 | 9/2014 | Shaw | |
| 2014/0276445 A1 | 9/2014 | Shaw et al. | |
| 2015/0073304 A1 | 3/2015 | Millerd | |
| 2016/0310057 A1* | 10/2016 | Shaw | A61B 5/150496 |
| 2016/0331909 A1 | 11/2016 | Shaw | |
| 2018/0008180 A1 | 1/2018 | Shaw et al. | |
| 2018/0008181 A1 | 1/2018 | Shaw et al. | |

\* cited by examiner

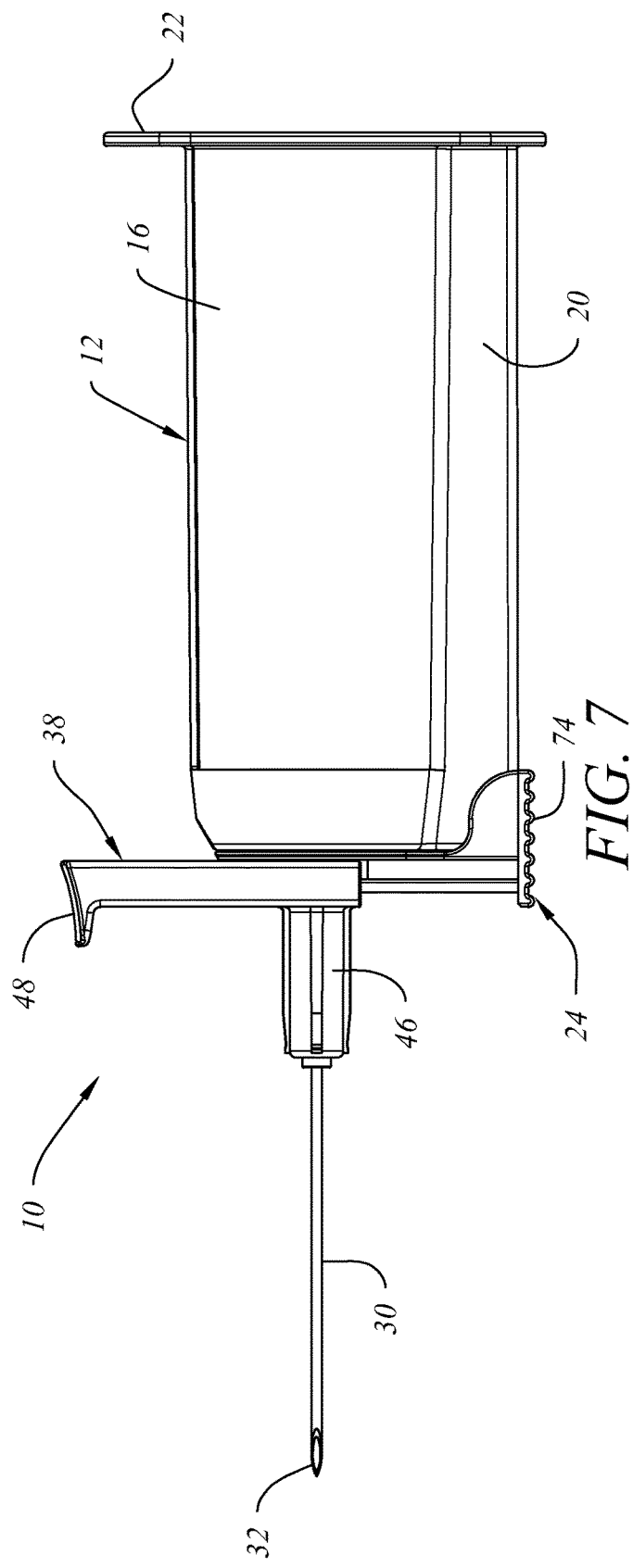
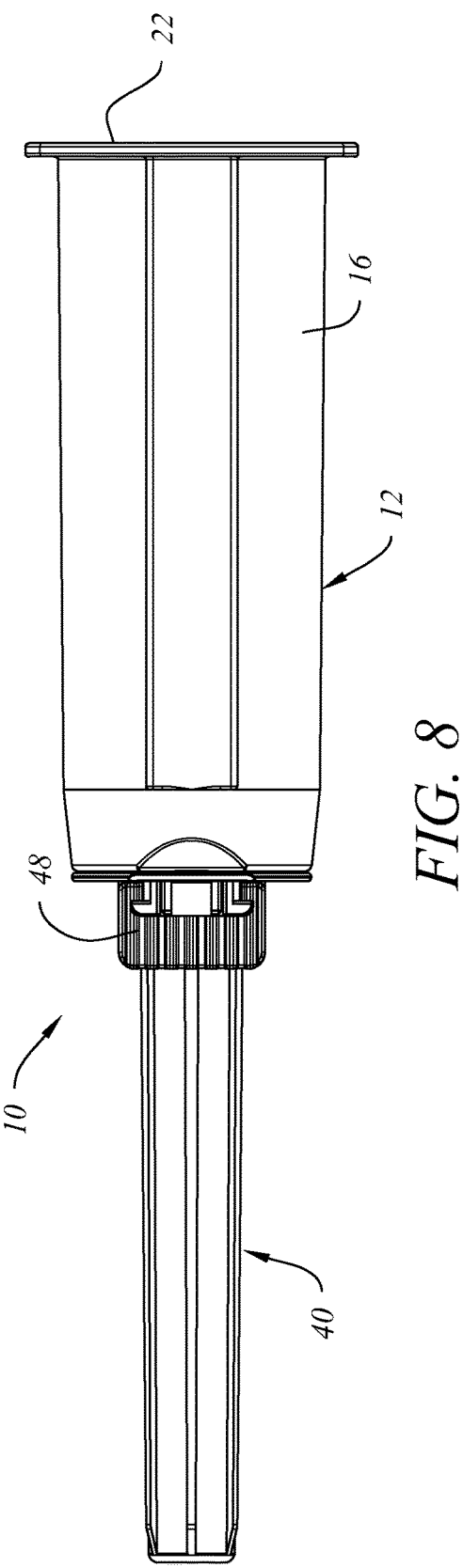
FIG. 7
FIG. 8

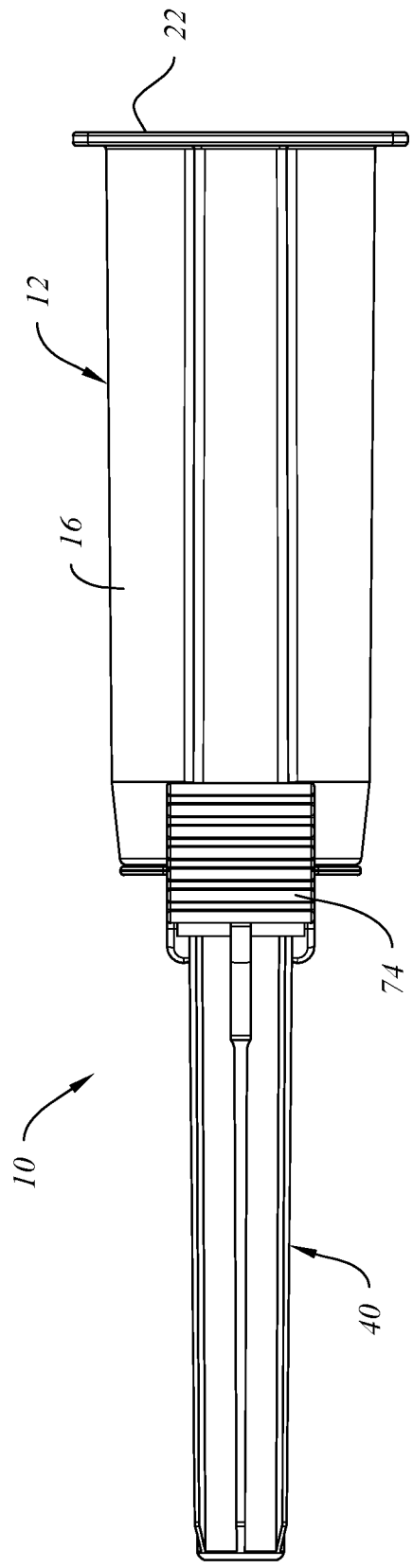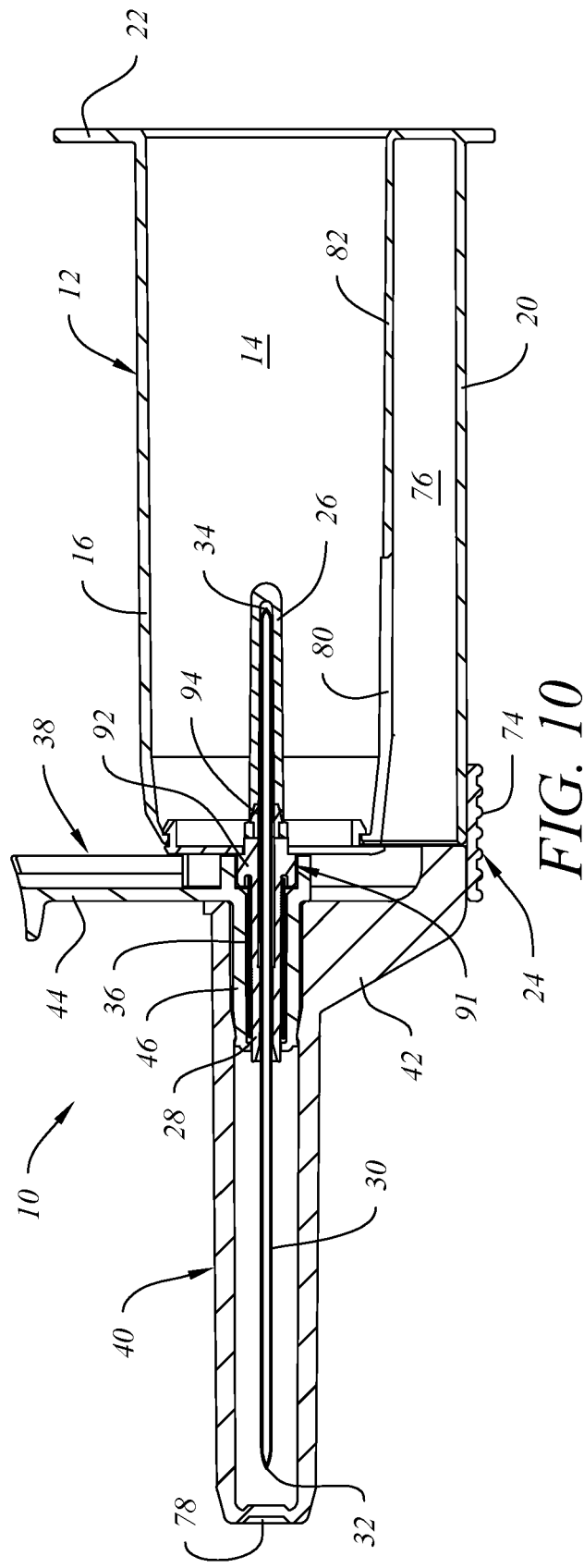

BLOOD COLLECTION TUBE HOLDER WITH SINGLE NEEDLE

1. FIELD OF THE INVENTION

This invention is a medical device useful for drawing blood from person or animal. The subject device is often referred to as a "blood collection tube holder" or "blood tube holder." because it is configured for use in combination with conventional, commercially available "blood collection tubes" or "blood tubes" that are manufactured and marketed by several different companies. The invention also relates to a single use blood collection tube holder having a single needle that is retractable into a confined space inside the device following use to protect a patient and healthcare workers from accidental needle sticks and thereby reduce the associated likelihood of pathogenic contamination resulting from an accidental stick. One aspect of the invention relates to a blood collection tube holder having a body comprising substantially parallel and laterally spaced apart barrel and needle retraction cavities separated by a partial wall that facilitates lateral movement of a retractable single needle from the barrel cavity into alignment with the needle retraction cavity to initiate needle retraction. Another aspect of the invention relates to a blood collection tube holder having a barrel and a frontal attachment that are cooperatively configured to facilitate relative sliding movement between them in a direction that is transverse to the longitudinal axis through the needle.

2. DESCRIPTION OF RELATED ART

Conventional blood collection tube holders are disclosed, for example, in U.S. Pat. No. 5,810,775; RE39, 107; 8,496, 600; 9,247,899 and in United States Publication Nos. 20160310057; 20180008180 and 2018/0008181.

Some such devices have two separate needles including a venipuncture needle pointing forwardly and a discharge needle pointing rearwardly. The discharge needle penetrates a stopper disposed in the front of a blood collection tube when the tube is inserted into the open rear end of a barrel. Following collection of a fluid sample, the blood collection tube is removed from the barrel of the blood tube holder, and a polymeric sheath expands to cover the rearwardly facing needle tip to prevent bodily fluid from leaking out the open back of the barrel. In one such device, a hinged cap is provided at the back of the barrel, and closing the cap following removal of the blood collection tube triggers retraction of both the discharge needle and the venipuncture needle rearwardly into the barrel, whereby the device is rendered "safe" and non-reusable.

More recently, blood collection tube holders have been disclosed that comprise a longer, rearwardly biased single needle having both forwardly and rearwardly facing pointed ends. Following collection of a fluid sample and removal of the blood collection tube, needle retraction is initiated by depressing an actuator containing a needle retraction cavity that is moved to a position where it is sufficiently aligned with the needle that both ends of the needle are biased backwardly into the needle retraction cavity of the device, whereby the device is rendered "safe" and non-reusable.

Even more recently, blood collection tube holders have been disclosed that comprise separate venipuncture and discharge needles, and a retraction cavity for the venipuncture needle that is disposed beside and parallel to the barrel, either as a separate chamber that is made integrally with the barrel or as part of a frontal attachment to the barrel. The venipuncture needle is rearwardly biased and retraction of the venipuncture needle is initiated by transverse sliding movement of at least part of the frontal attachment to the barrel. During such movement the forwardly projecting venipuncture needle is moved laterally out of alignment with the rearwardly facing discharge needle into substantially coaxial alignment with the needle retraction cavity. Once the venipuncture needle is substantially aligned with the needle retraction cavity, the rearwardly directed biasing force causes the venipuncture needle to be withdrawn to a "safe" position inside the device while the discharge needle remains disposed in its original position inside the barrel. Either before or after needle retraction, the blood collection tube can be removed from the barrel, and an elastomeric sheath expands over the rearwardly facing tip of the discharge needle to prevent bodily fluid from leaking out the open rear end of the barrel.

Notwithstanding the improvements and advantages achieved through use of the previously disclosed devices, a blood collection tube hold is needed that comprises a single needle which can be retracted following use by lateral sliding movement of a frontal attachment relative to the barrel to reposition the whole needle into substantially coaxial alignment with a full-length needle retraction cavity that is made integrally with the barrel.

SUMMARY OF THE INVENTION

A blood collection tube holder is disclosed that comprises a substantially cylindrical body, a frontal attachment, and a retractable single needle comprising oppositely directed venipuncture and fluid discharge ends or tips. The body and the frontal attachment are cooperatively configured to facilitate sliding lateral movement of the body relative to the single needle prior to needle retraction. In one satisfactory embodiment of the invention, the body further comprises a substantially cylindrical barrel cavity and an integrally formed needle retraction cavity that are substantially parallel and separated by a partial wall. The partial wall is desirably configured to facilitate sliding lateral movement of the fluid discharge end of the single needle from a first position where it is substantially centered inside of and coaxially aligned with the barrel cavity to a second position where it is substantially aligned with the needle retraction cavity. The barrel cavity is configured to receive and support a conventional blood collection tube in operative engagement with the fluid discharge end of the single needle.

The venipuncture end of the single needle projects forwardly from the frontal attachment and is desirably covered by a selectively releasable needle cap prior to use. The frontal attachment further comprises a tube holder connector that frictionally engages and partially covers the open front end of the barrel, and a slide member that slidably engages the tube holder connector along an axis that is substantially transverse to the longitudinal axis through the single needle. The slide member is configured to seat and support a rearwardly biased needle holder attached in fixed relation to the single needle. The tube holder connector further comprises a transverse slot that facilitates relative lateral movement of the single needle between the first and second positions when oppositely directed manual pressure is applied to the body and slide member for the purpose of substantially aligning the needle holder and needle retraction cavity to initiate retraction of the single needle into the needle retraction cavity. In one preferred embodiment of the invention, the selectively releasable needle cap further comprises a locking arm that prevents the slide member and the needle retraction cavity from becoming substantially aligned and thereby initiating retraction of the single needle prior to use.

BRIEF DESCRIPTION OF THE DRAWINGS

The apparatus of the invention is further described and explained in relation to the following drawings wherein:

FIG. 7 is a top plan view of the blood collection tube holder of FIG. 4 with the needle cap removed;

FIG. 8 is a right side elevation view of the blood collection tube holder of FIGS. 1 and 3;

FIG. 9 is a left side elevation view of the blood collection tube holder of FIG. 1 rotated 180 degrees in a clockwise direction around its longitudinal axis;

FIG. 10 is a cross-sectional view taken along line 10-10 of FIG. 5;

DESCRIPTION OF THE PREFERRED EMBODIMENTS

Figure 1:
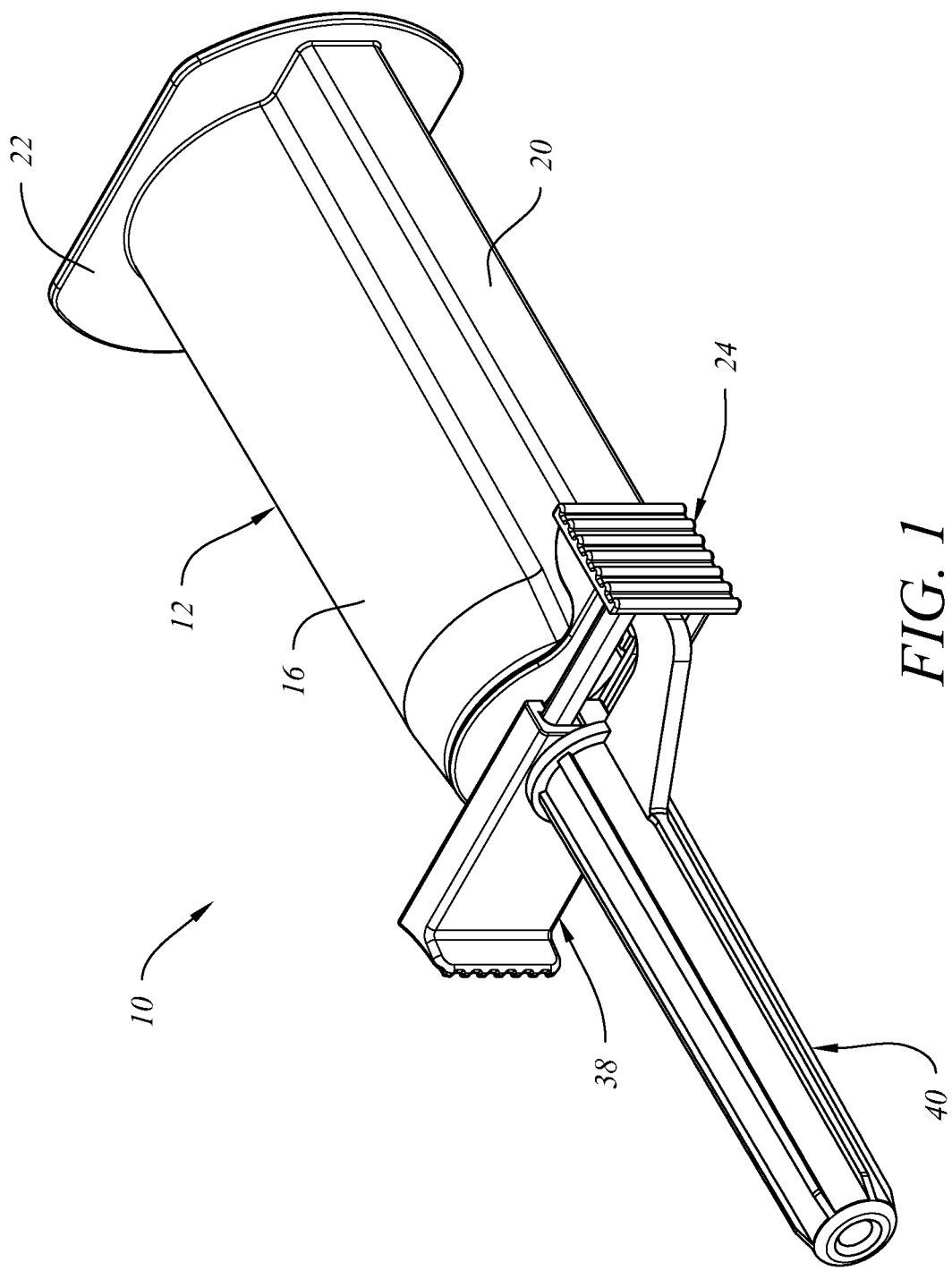
FIG. 1 is a front perspective view of one embodiment of the blood collection tube holder of the invention.
Figure 2:
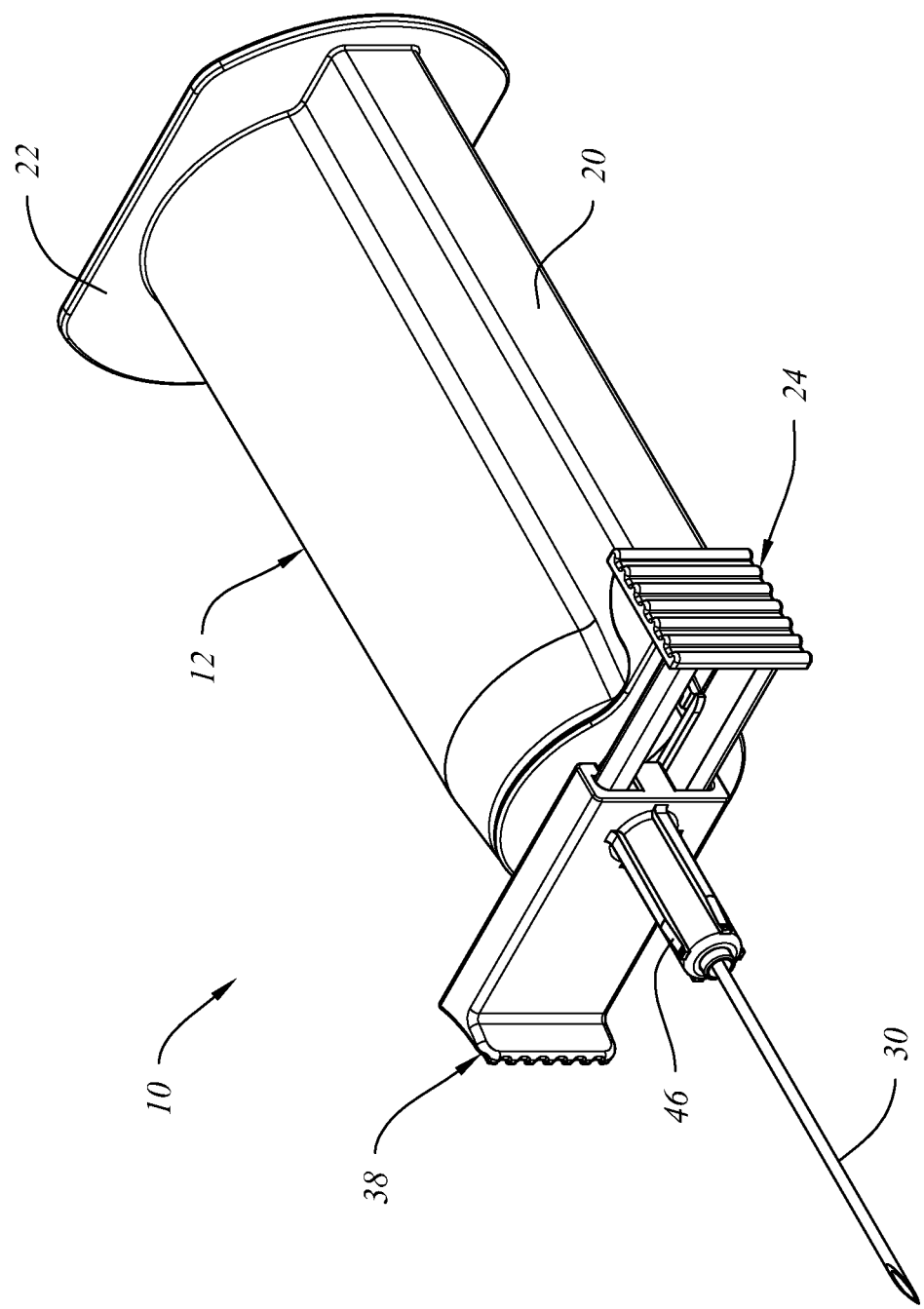
FIG. 2 is a front perspective view of the blood collection tube holder of FIG. 1 with the needle cap removed.
Figure 3:
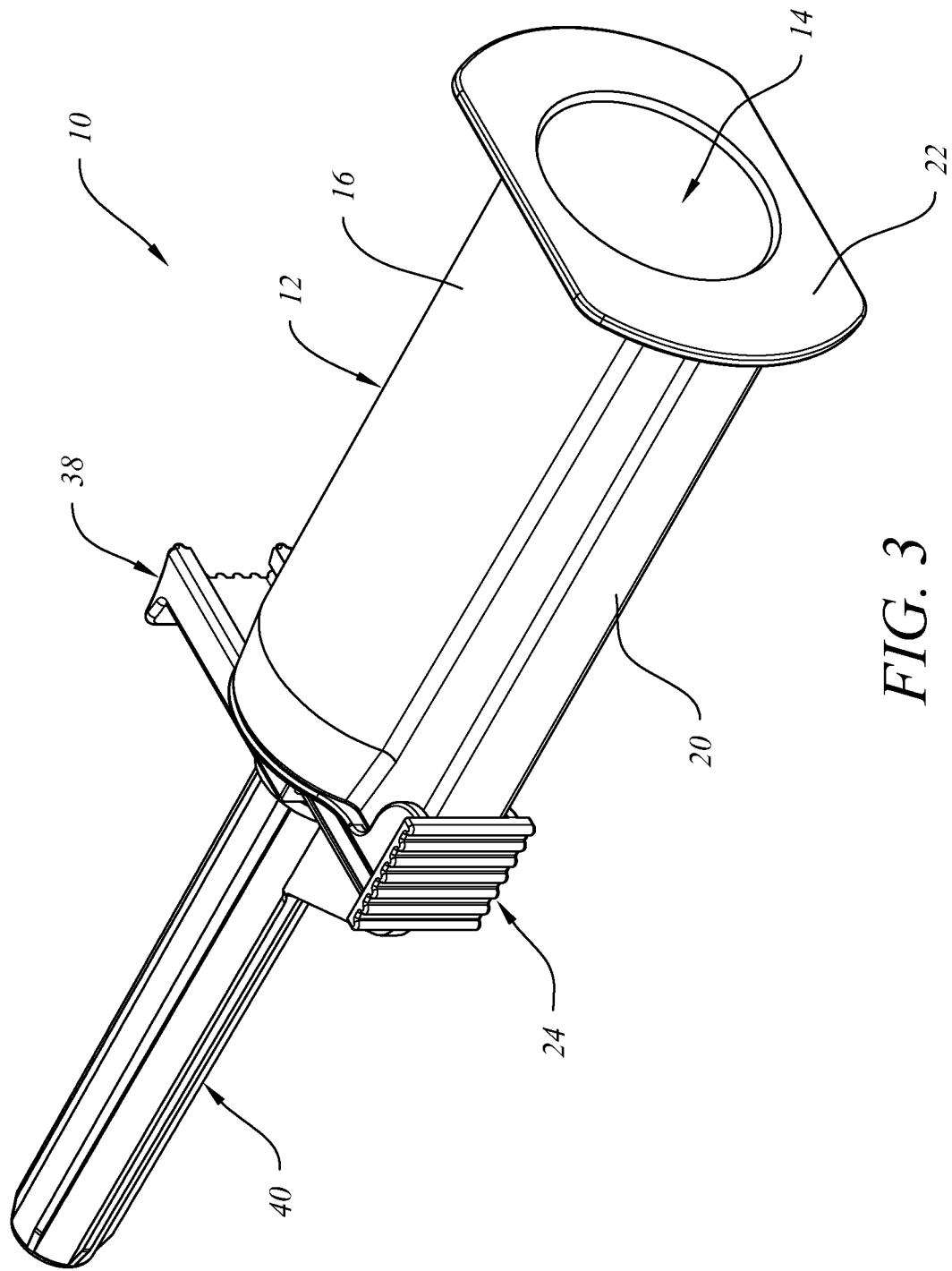
FIG. 3 is a rear perspective view of the blood collection tube holder of FIG. 1.
Figure 4:
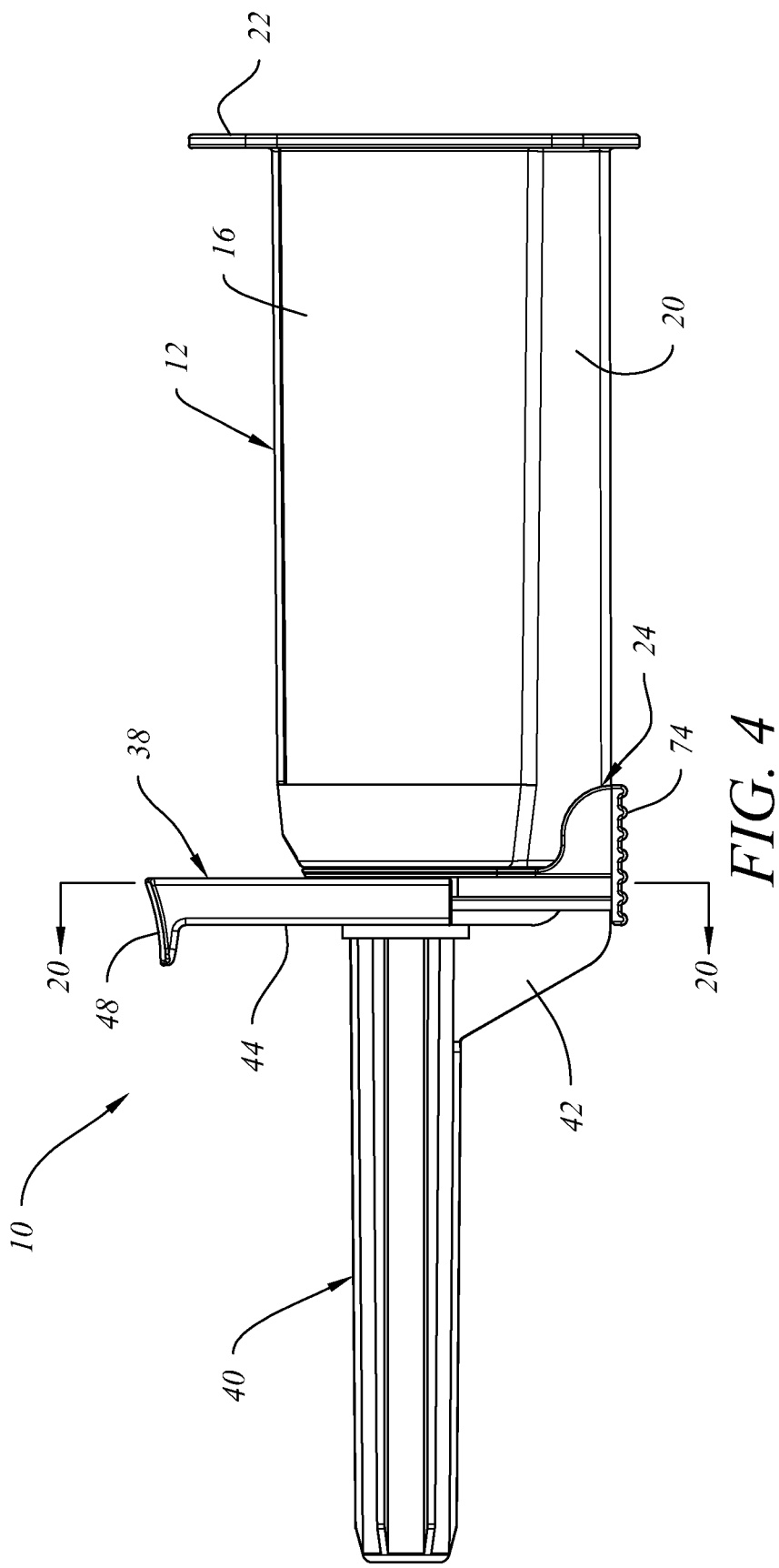
FIG. 4 is a top plan view of a blood collection tube holder substantially as shown in FIGS. 1 and 3 except that indicia are also shown in dashed outline in FIG. 4.

Referring to FIGS. 1-11 and 14, blood collection tube holder 10 comprises body 12, a frontal attachment further comprising tube holder connector 24 and slide member 38, needle cap 40 (FIGS. 1 and 3) FIGS. 1, 3-5 and 8-11), and retractable single needle 30 (FIGS. 2, 7, 10, 11 and 14). Body 12 further comprises barrel 16, barrel cavity 14, needle retraction chamber 20 and rear flange 22 disposed around the rear opening of barrel 16. Referring to FIGS. 2 and 7, retractable single needle 30 projects forwardly from needle support member 46 of slide member 38 of the frontal attachment.

Referring to FIGS. 4-6 and 8-10, blood collection tube holder 10 is depicted in its pre-use position in which selectively removable needle cap 40 with closed front end 78 (FIG. 10) is installed over retractable single needle 30 and frictionally engages axially extending, circumferentially spaced ribs disposed around needle support member 46 (visible in FIG. 7). Locking support arm 42 (visible in FIGS. 10-11) is provided to prevent relative sliding movement between body 12 and slide member 38 prior to using retractable single needle 30 to draw blood from a patient. Slide member 38 further comprises front surface 44 from which needle support member 46 projects forwardly around part of retractable single needle 30 as best seen in FIG. 7.

Figure 11:
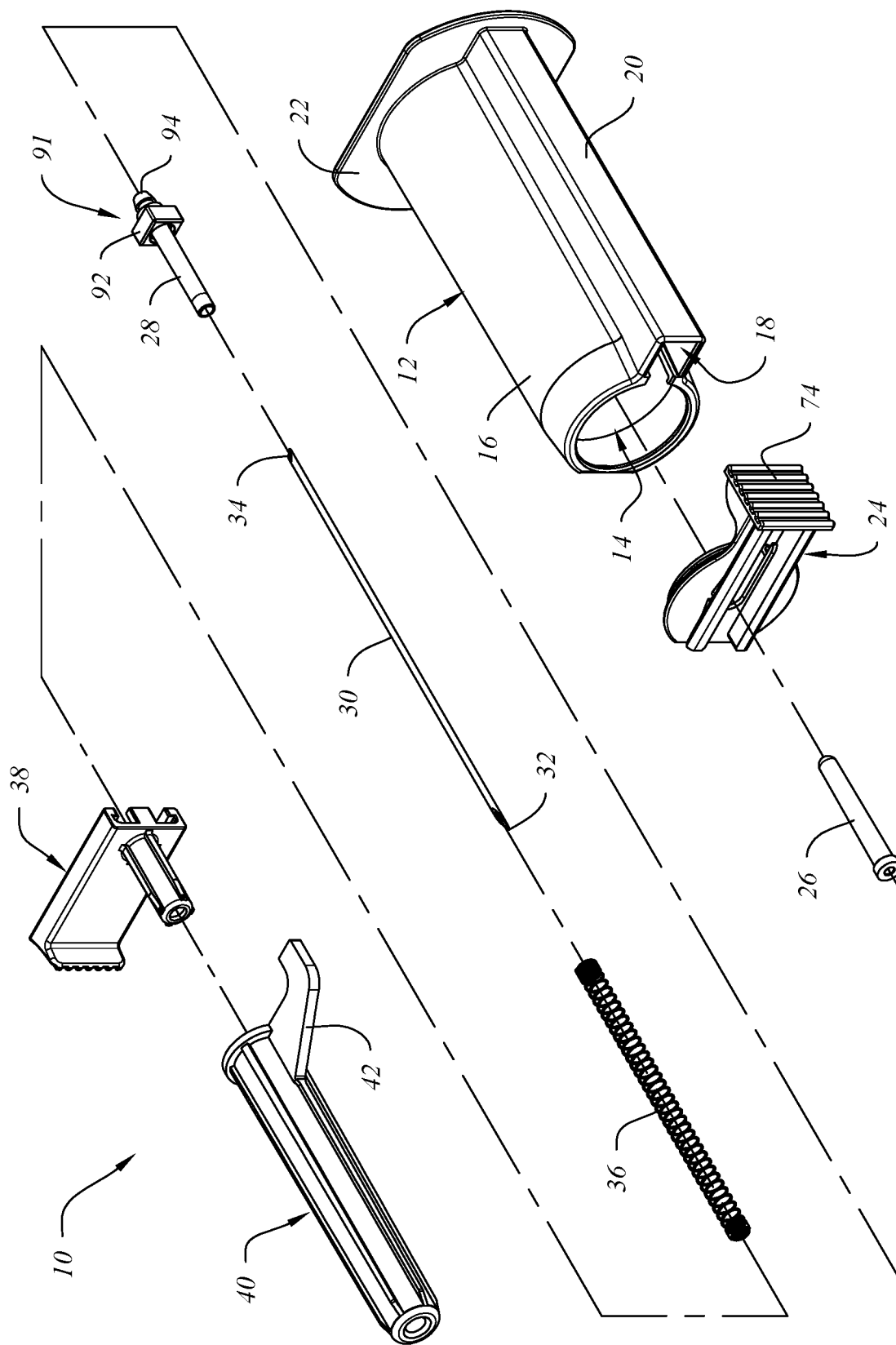
FIG. 11 is an exploded perspective view of the blood collection tube holder of FIG. 1.
Figure 12:
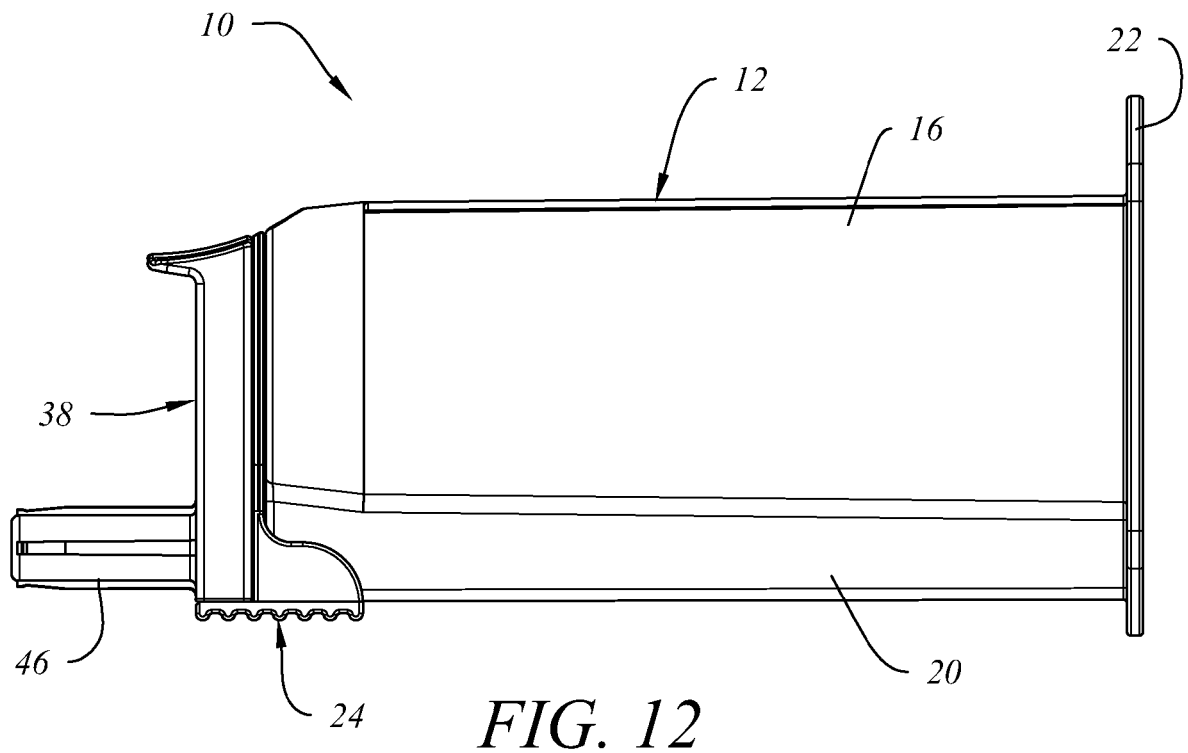
FIG. 12 is the blood collection tube holder of FIG. 7 with the venipuncture needle retracted.

Referring to FIGS. 10-11, retractable single needle 30 further comprises forwardly facing venipuncture end 32 and rearwardly facing fluid discharge end 34. Prior to insertion of a blood collection tube (not shown) into barrel cavity 14 and use of blood collection tube holder 10 for collecting blood from a patient, selectively releasable needle cap 40 is in place as discussed above, and collapsible elastomeric sheath 26 covers fluid discharge end 34 of retractable single needle 30 to shield fluid discharge end 34 from inadvertent contamination. When a blood collection tube is inserted into barrel cavity 14 of barrel 16 of body 12, collapsible elastomeric sheath 26 is collapsed rearwardly around retractable single needle 30, allowing fluid discharge end 34 to penetrate an elastomeric stopper in the blood collection tube to establish fluid communication between venipuncture end 32 of retractable single needle 30 and the inside of the blood collection tube into which the drawn blood is discharged. When single retractable needle 30 is in its pre-use position as shown in FIG. 10, needle 30 is substantially centered inside barrel cavity 14 and is laterally spaced apart from needle retraction cavity 76 inside needle retraction chamber 20 of body 12.

Figure 16:
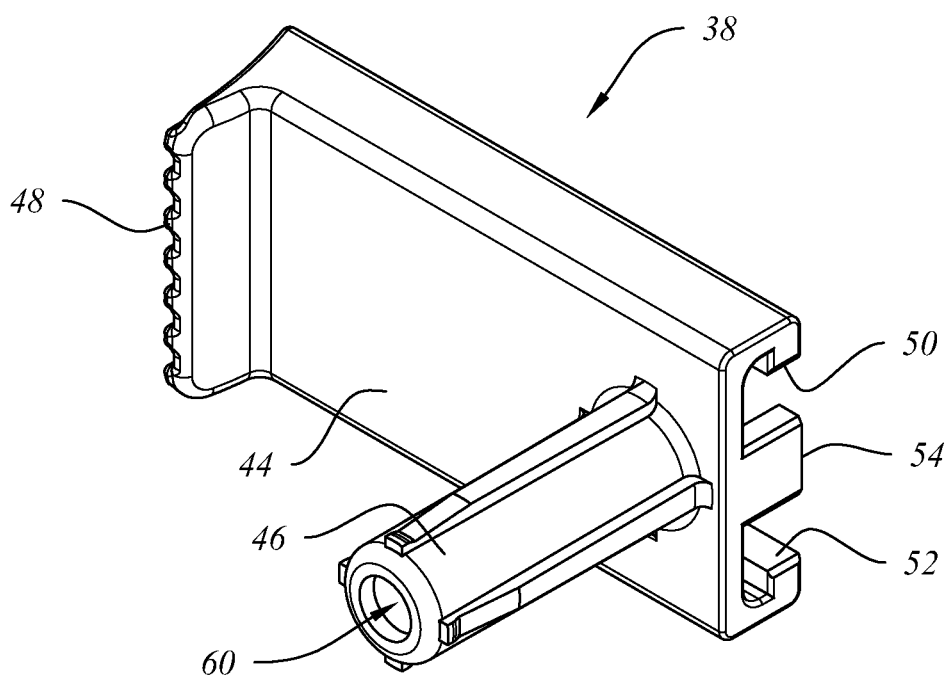
FIG. 16 is an enlarged detail view of the needle support member of FIG. 11.

Referring again to FIGS. 10-11, retractable single needle 30 is desirably attached in fixed axial relation to needle holder 91, which further comprises forwardly facing shaft portion 28, head 92 and a rearwardly extending annular projection 94 provided for use in frictionally engaging the forwardly extending end of collapsible elastomeric sheath 26, which is preferably a rubber sleeve. A biasing member such as compressible coiled spring 36 is desirably seated inside bore 60 (FIG. 16) of needle support member 46 around a centrally disposed portion of needle 30 and forwardly facing shaft portion of needle holder 91, and when compressed during assembly of blood collection tube holder 10, abuts and engages the front side of head 92 of needle holder 91. For so long as retractable single needle 30 remains in its forwardly projecting position, head 92 of needle holder 91 is biased rearwardly relative to the frontal attachment and body 12 of blood collection tube holder 10.

Figure 17:
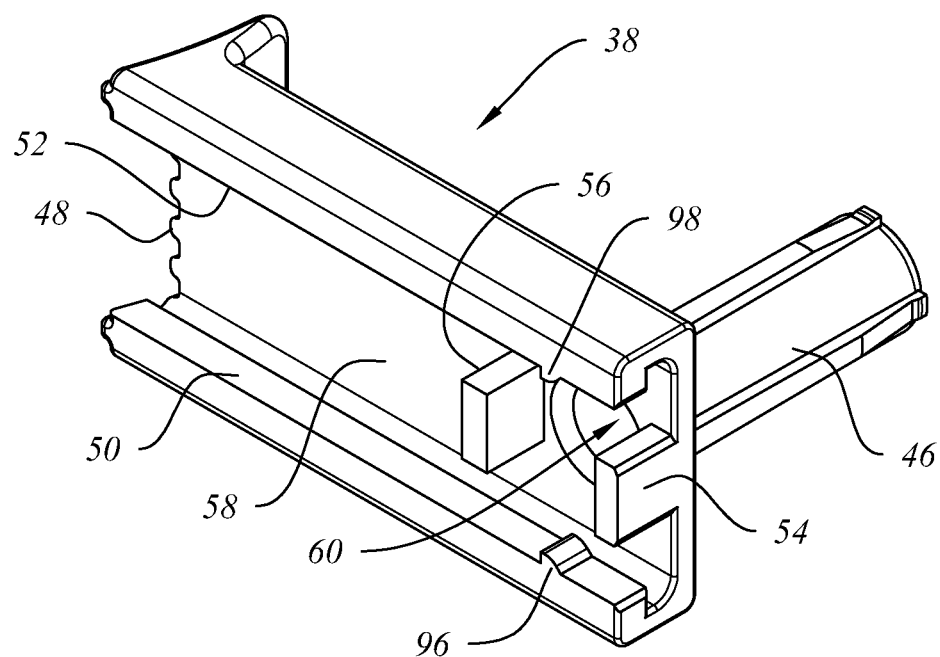
FIG. 17 is a rear perspective view of the needle support member of FIG. 16 rotated 180 degrees in a clockwise direction around the longitudinal axis through the subject blood collection tube holder.
Figure 18:
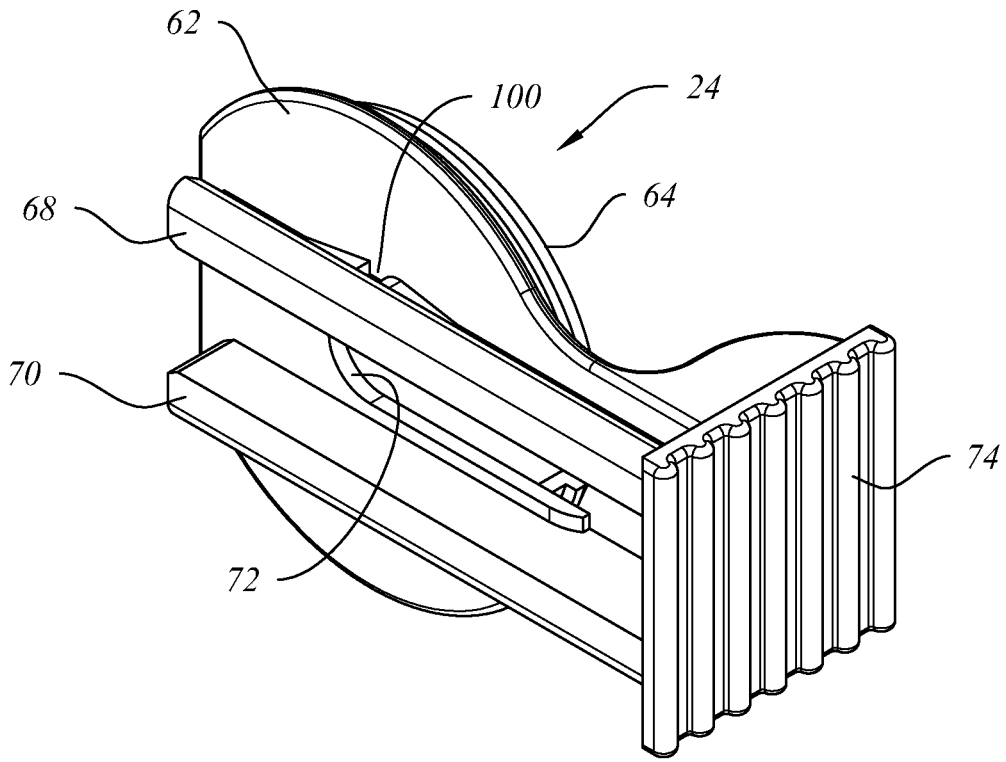
FIG. 18 is an enlarged detail view of the tube holder connector of FIG. 11.

Referring to FIGS. 11, 16-17 and 20, slide member 38 of the frontal attachment to body 12 (FIG. 7) further comprises opposed positioning blocks 54, 56 that are engageable with cooperatively configured head 92 of needle holder 91 (FIG. 11) to move needle holder 91 laterally as discussed below. Laterally extending top and bottom rails 50, 52, respectively, are cooperatively configured and slidably engageable with laterally extending top and bottom rails 68, 70 of tube holder connector 24. Referring to FIGS. 17-18, projections 96, 98 (FIG. 17) on slide member 38 are desirably provided to engage cooperatively configured and aligned recesses 100

Figure 19:
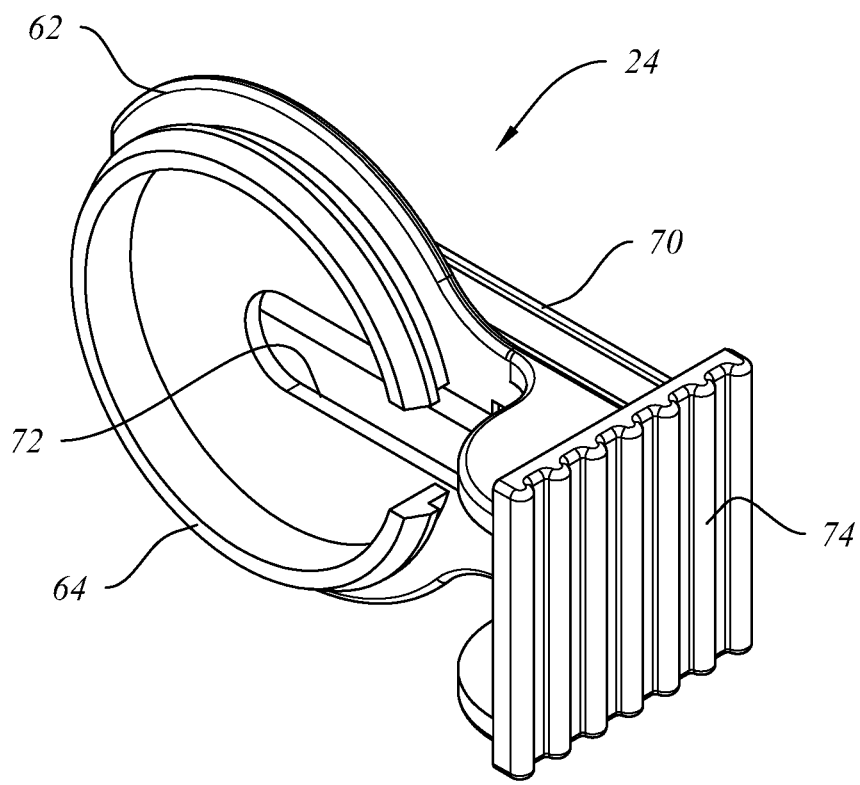
FIG. 19 is a rear perspective view of the tube holder connector of FIG. 18 rotated 180 degrees in a clockwise direction around the longitudinal axis through the subject blood collection tube holder.
Figure 20:
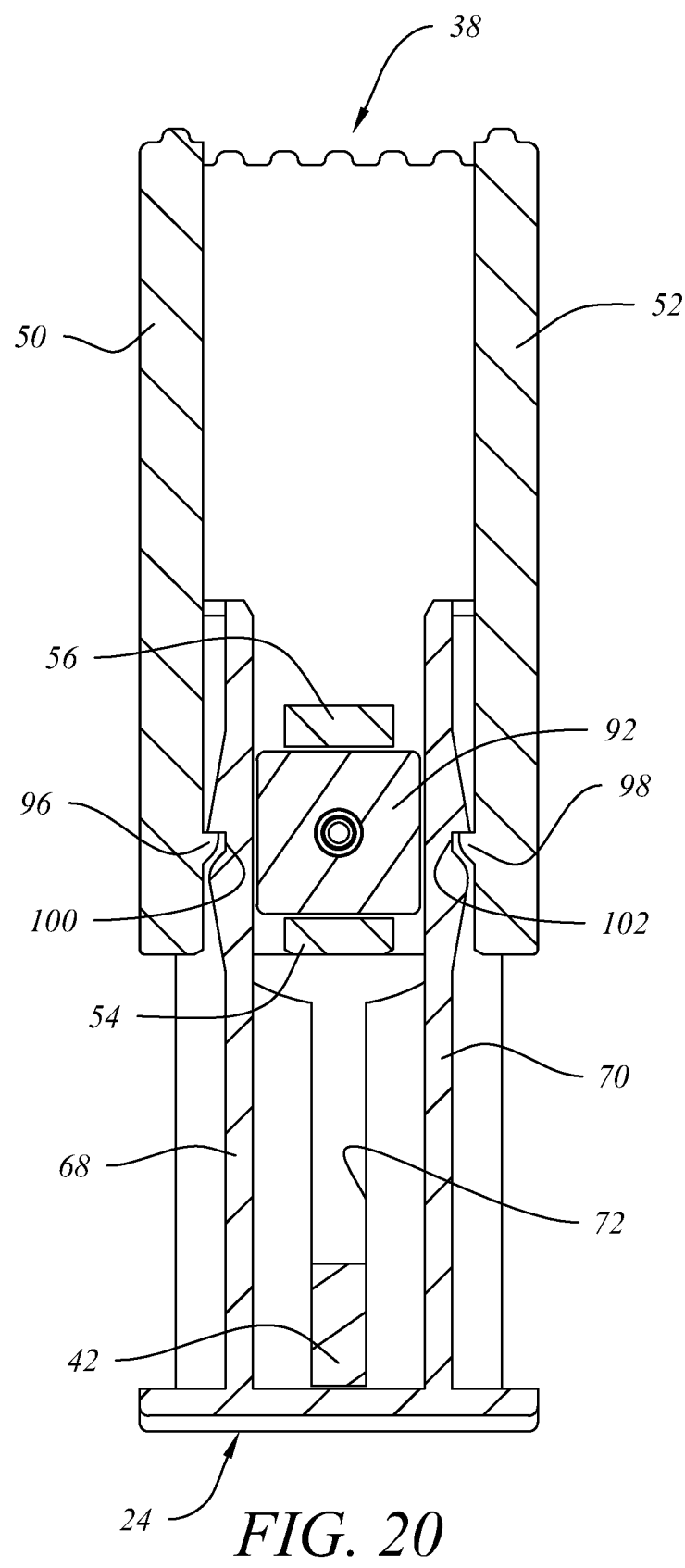
FIG. 20 is an enlarged cross-sectional view taken along line 20-20 of FIG. 4.

(bottom recess not visible) of tube holder connector 24 to properly position retractable single needle 30 within slot 72 of tube holder connector 24 during assembly and use of blood collection tube holder 10. Referring to FIGS. 11,18-19, circumferentially extending arcuate ring 64 and cooperating circular wall 62 of tube holder connector 24 are provided to establish frictional engagement between tube holder connector 24 and the forwardly facing edge of barrel 16 of body 12. The frictional engagement is desirably sufficient that tube holder connector 24 remains attached to the front end of barrel 16 as oppositely directed pressure is applied to textured touch surfaces 74, 48 as discussed below.

Figure 5:
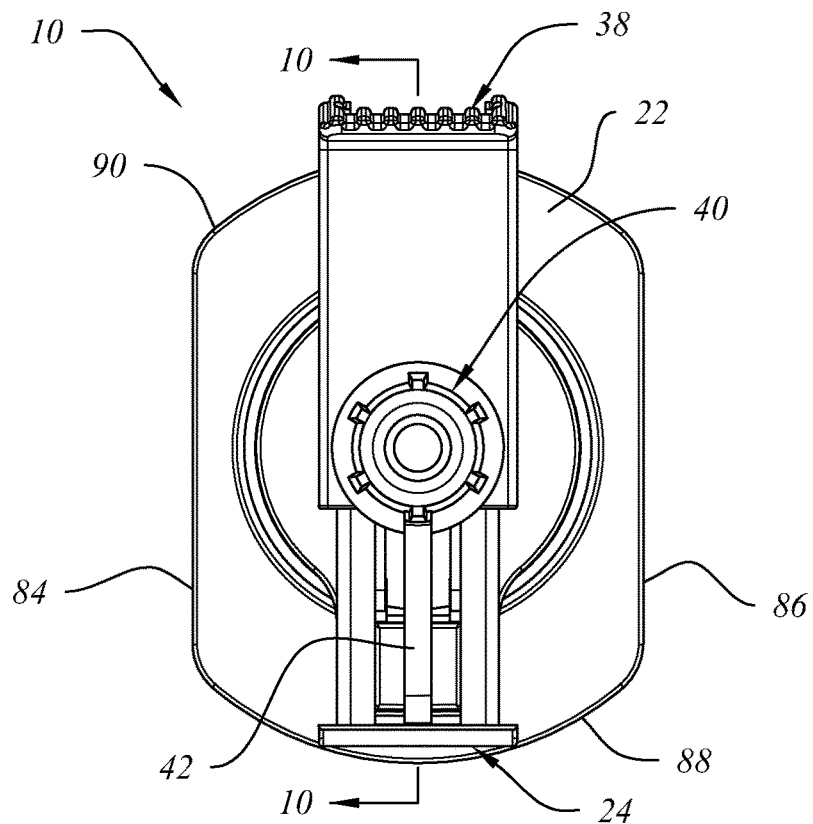
FIG. 5 is a front view of the blood collection tube holder of FIG. 1 but rotated 90 degrees in a clockwise direction around its longitudinal axis.
Figure 6:
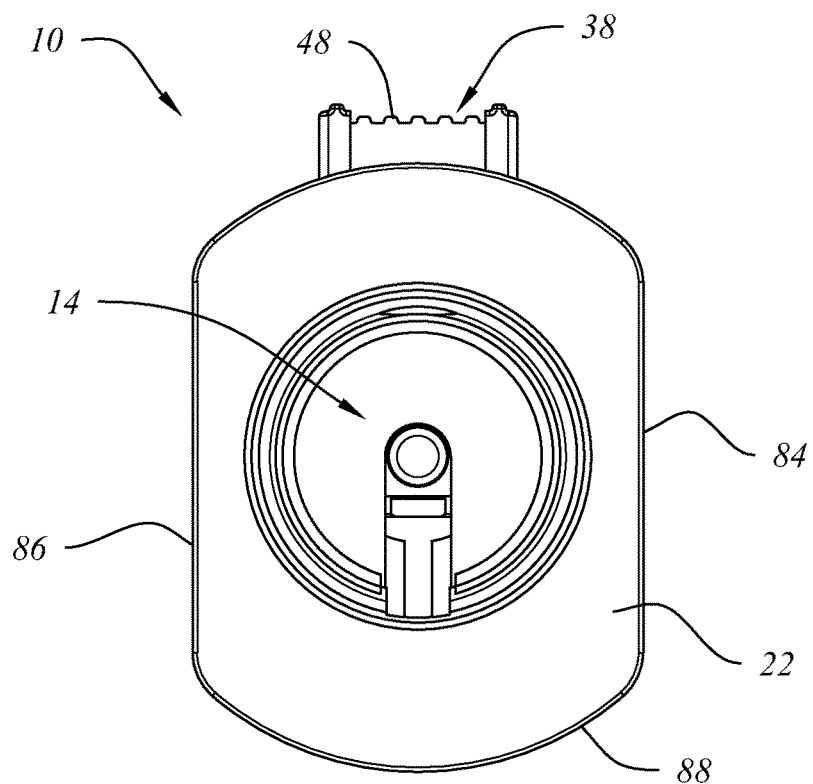
FIG. 6 is a rear view of the blood collection tube holder of FIG. 5.
Figure 13:
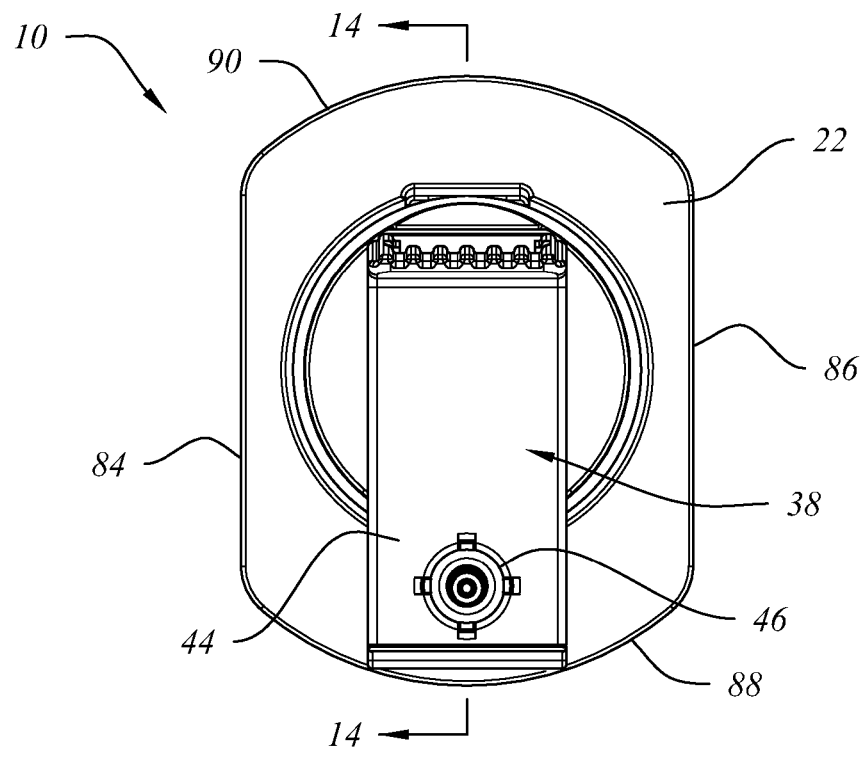
FIG. 13 is the blood collection tube holder of FIG. 5 with the needle cover removed and the venipuncture needle retracted.

FIGS. 5-6 and 13 further depict opposed flat edges 84, 86 in relation to opposed arcuate edges 88, 90 of flange 22 and the relative positions of slide member 38 and tube holder connector 24 whenever needle 30 is in the unretracted and retracted positions, respectively.

Figure 14:
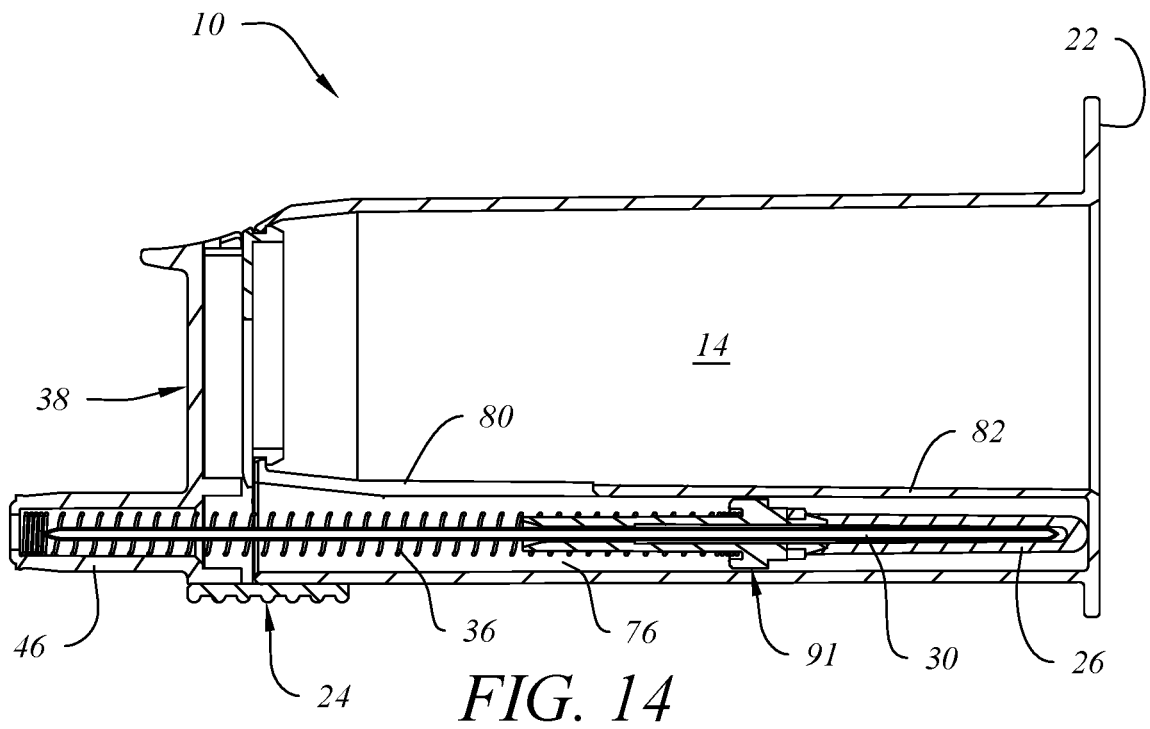
FIG. 14 is a cross-sectional view taken along line 14-14 of FIG. 13.
Figure 15:
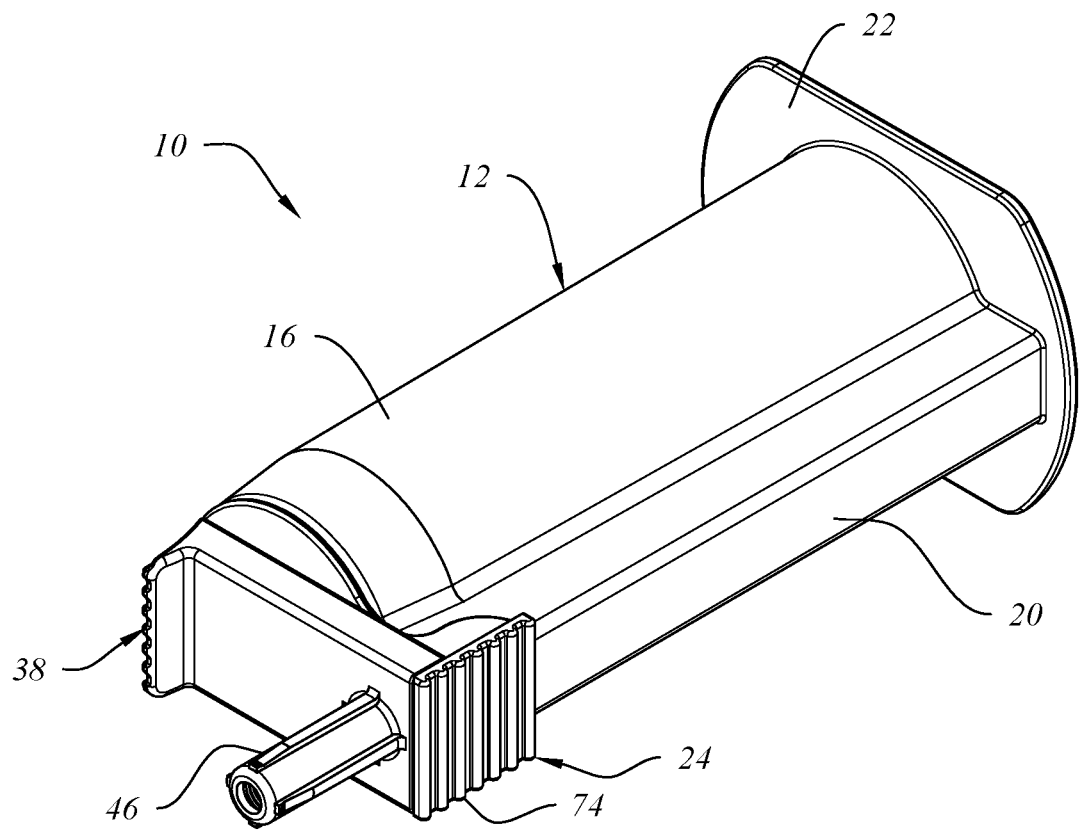
FIG. 15 is the blood collection tube holder of FIG. 2 with the needle retracted.

Referring to FIGS. 5, 7-11 and 14-15, slide member 38 and tube holder connector 24 of the frontal attachment to body 12 are provided with textured touch pads 48, 74, respectively, to facilitate the application of oppositely directed manual pressure to each touch pad to produce lateral sliding movement of body 12 relative to slide member 34, needle holder 91, compression spring 36 and retractable single needle 30. This movement is desirably in a transverse direction that causes discharge needle end 34 of retractable single needle 30 to move laterally past reduced height portion 80 of partial wall 82 (FIG. 10) until needle 30 is substantially aligned with needle retraction cavity 76, which allows needle holder 91 and discharge needle end 34 to move rearwardly into needle retraction cavity 76 as compressed coil spring 36 expands to the position shown in FIG. 14. The length of retractable single needle 30 is desirably such that venipuncture end 32 of needle 30 is fully contained inside needle support member 46 of slide member 38 when in the position as shown in FIG. 14. FIGS. 12-15 depict blood collection tube holder 10 of the invention with retractable single needle 30 in the fully retracted position.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventor and/or Applicant are legally entitled.

What is claimed is:

1. A blood collection tube holder, comprising:
   a body comprising a barrel and a needle retraction cavity, wherein the barrel and the needle retraction cavity are integrally formed, substantially parallel, and separated by a partial wall;
   a tube holder connector coupled to a forwardly facing end of the barrel and comprising a transverse slot;
   a slide member slidably engaging the tube holder connector; and
   a rearwardly biased, retractable needle assembly comprising a needle holder and a single needle having a venipuncture portion extending forwardly from the needle holder, through the transverse slot of the tube holder connector, and projecting forwardly from the slide member and a fluid discharge portion extending rearwardly from the needle holder within the barrel;
   wherein lateral sliding movement of the slide member with respect to the tube holder connector and the barrel causes the venipuncture portion to slide transversely through the transverse slot of the tube holder connector and the fluid discharge portion of the single needle to slide laterally past the partial wall until the single needle is aligned with the needle retraction cavity, which initiates retraction of the needle assembly within the needle retraction cavity.

2. The blood collection tube holder of claim 1, wherein the tube holder connector comprises a circumferentially extending ring that frictionally engages the forwardly facing end of the barrel.

3. The blood collection tube holder of claim 2, wherein the slide member slidably engages the tube holder connector along an axis that is substantially transverse to a longitudinal axis through the retractable single needle.

4. The blood collection tube holder of claim 3, wherein the transverse slot of the tube holder connector facilitates relative lateral movement of the retractable single needle to initiate retraction when oppositely directed manual pressure is applied to the tube holder connector and the slide member.

5. The blood collection tube holder of claim 1, wherein the slide member comprises a needle support member that receives a spring to rearwardly bias a needle holder that secures in fixed relation the retractable single needle.

6. The blood collection tube holder of claim 1, wherein the tube holder connector is frictionally engaged with an open front end of the barrel.

7. The blood collection tube holder of claim 1, wherein the slide member and the tube holder connector slidably engage along a pair of cooperatively configured rails.

8. The blood collection tube holder of claim 1, wherein the slide member and the tube holder connector comprise textured touch pads to facilitate application of oppositely directed manual pressure to laterally slide the slide member with respect to the tube holder connector and the barrel.

9. The blood collection tube holder of claim 1, wherein the needle holder affixes the single needle in fixed relation to the needle holder.

10. The blood collection tube holder of claim 9, wherein the needle holder is rearwardly biased by a spring received within a needle support member of the slide member.

11. The blood collection tube holder of claim 1, wherein the barrel and the needle retraction cavity are in fluid communication via a reduced height portion of the partial wall.

12. The blood collection tube holder of claim 1, wherein the venipuncture portion of the single needle is fully contained within the needle support member of the slide member when the needle assembly is retracted.

13. The blood collection tube holder of claim 12, wherein a needle holder of the needle assembly and the fluid discharge portion of the single needle are received within the needle retraction cavity upon retraction of the needle assembly.

14. The blood collection tube holder of claim 1, wherein a rearwardly facing end of the fluid discharge portion of the single needle retracts longitudinally beyond the partial wall.

15. A blood collection tube holder, comprising:
   a body comprising a barrel and an integrally formed needle retraction chamber;
   a tube holder connector coupled to the barrel;
   a slide member slidably engaging the tube holder connector; and
   a retractable single needle comprising a venipuncture portion and a fluid discharge portion;
   wherein the barrel comprises a barrel cavity, wherein the needle retraction chamber comprises a needle retraction cavity, and wherein the barrel cavity and the needle retraction cavity are disposed in a fixed, substantially parallel relationship and separated by a partial wall; and wherein the tube holder connector comprises a transverse slot configured to allow lateral sliding movement of the venipuncture portion of the retractable single needle therethrough while projecting forwardly from the slide member and the partial wall comprises a reduced height portion configured to simultaneously allow lateral sliding movement of the fluid discharge portion of the retractable single needle past the reduced height portion of the partial wall from a first position where the retractable single needle is coaxially aligned with the barrel cavity to a second position where the retractable single needle is coaxially aligned with the needle retraction cavity to initiate retraction of the retractable single needle within the needle retraction chamber.

16. The blood collection tube holder of claim 15, wherein the venipuncture portion of the retractable single needle projects forwardly from the slide member prior to needle retraction.

17. The blood collection tube holder of claim 15, wherein the venipuncture portion of the retractable single needle is covered by a selectively releasable needle cap prior to use.

18. The blood collection tube holder of claim 17, wherein the selectively releasable needle cap further comprises a locking arm that prevents the slide member and the needle retraction cavity from becoming substantially aligned prematurely and thereby initiating needle retraction prior to use of the blood collection tube holder for drawing blood.

19. The blood collection tube holder of claim 15, wherein the retractable single needle is affixed in a needle holder that is rearwardly biased by a spring received within a needle support member of the slide member, and wherein a rearwardly facing end of the fluid discharge portion of the retractable single needle retracts longitudinally beyond the reduced height portion of the partial wall.

* * * * *